United States Patent [19]
Johnson

[11] Patent Number: 6,149,654
[45] Date of Patent: *Nov. 21, 2000

[54] INTRA-ARTICULAR DRILL

[76] Inventor: Lanny L. Johnson, 2950 E. Mount Hope Rd., Okemos, Mich. 48864

[ * ] Notice: This patent issued on a continued prosecution application filed under 37 CFR 1.53(d), and is subject to the twenty year patent term provisions of 35 U.S.C. 154(a)(2).

[21] Appl. No.: 09/082,465

[22] Filed: May 21, 1998

[51] Int. Cl.$^7$ ..................................................... A61B 17/00
[52] U.S. Cl. ............................................................. 606/80
[58] Field of Search ................................. 606/80, 79, 85, 606/73, 104; 408/180, 223, 231, 227, 229, 230, 713; 279/93

[56] References Cited

U.S. PATENT DOCUMENTS

| | | | |
|---|---|---|---|
| 5,330,480 | 7/1994 | Meloul et al. | 606/80 |
| 5,470,334 | 11/1995 | Ross et al. | 606/72 |
| 5,499,984 | 3/1996 | Steiner et al. | 606/80 |
| 5,569,252 | 10/1996 | Justin et al. | 606/73 |
| 5,645,547 | 7/1997 | Coleman | 606/73 |
| 5,658,289 | 8/1997 | Boucher et al. | 606/73 |
| 5,713,905 | 2/1998 | Goble et al. | 606/80 |
| 5,755,718 | 5/1998 | Sklar | 606/80 |

*Primary Examiner*—Michael Buiz
*Assistant Examiner*—(Jackie) Tan-Uyen Thi Ho
*Attorney, Agent, or Firm*—Pillsbury Madison & Sutro LLP

[57] ABSTRACT

A drill bit is dimensioned to be received within a bone joint. The bit is oriented and retained in position by a removable fixation device to permit a drill drive shaft to be secured to, or removed from, the drill bit. By securing the drive shaft within a cavity at the end of the bit which performs the drilling function, retrograde drilling of bone from within the joint can be achieved. When the drive shaft is secured within a cavity at the opposite end of the drill bit, antegrade drilling of bone is possible from within the joint.

4 Claims, 3 Drawing Sheets

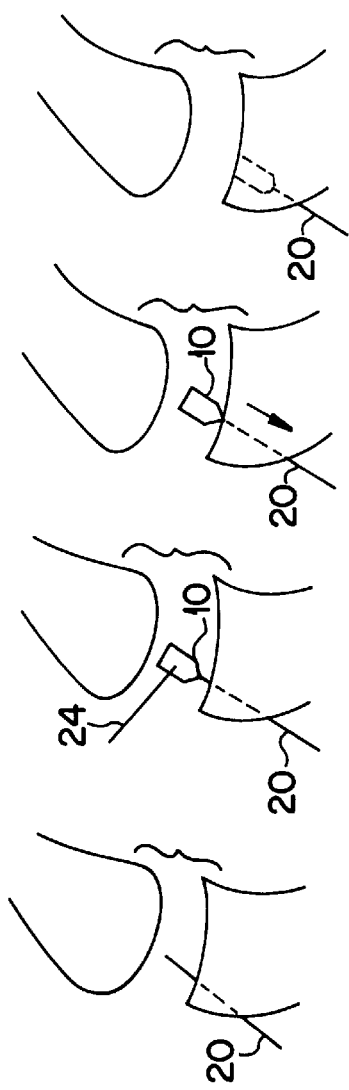
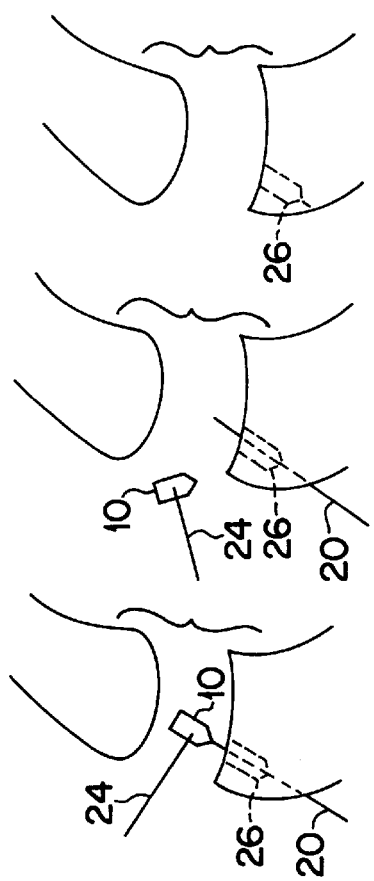

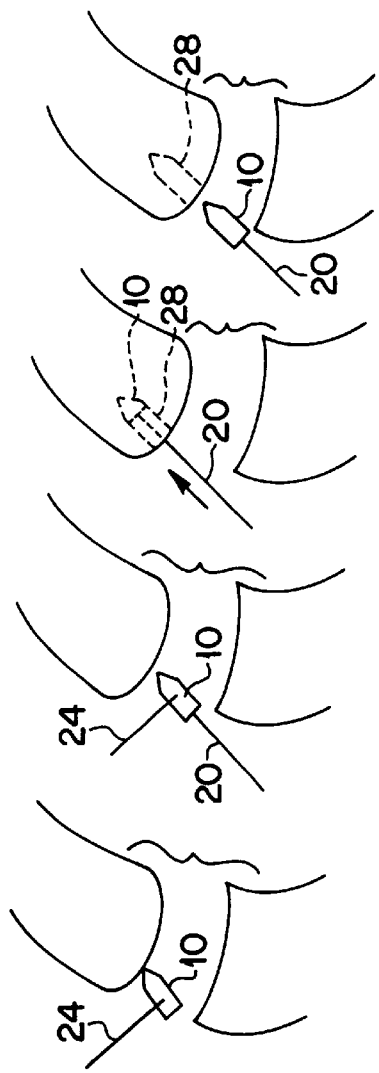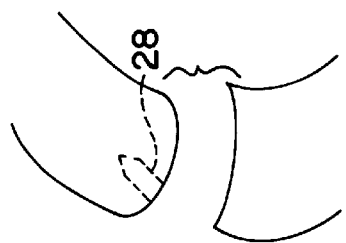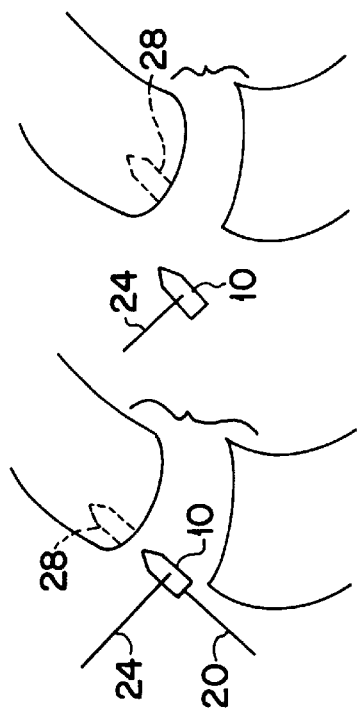

INTRA-ARTICULAR DRILL

BACKGROUND OF THE INVENTION

1. Field of the Invention

The present invention relates to a medical instrument which allows a drill hole to be placed in bone from within a joint. The drill hole can be formed in either an antegrade or retrograde fashion.

2. The Prior Art

In various types of orthopaedic surgical procedures it is necessary to form a drill hole in bone at a position within a joint. Typically, this is accomplished by a conventional drill which is deployed in such a way that it enters the joint by a drilling operation initiated from outside the joint. Thus, bone and/or tissue located between the drill bit and the joint is removed in an amount corresponding to the size of the drill bit. Such a procedure is more invasive than that required to implement use of the present invention.

SUMMARY OF THE INVENTION

The present invention is an intra-articular drill wherein a drill bit is sized so that it can be manually implanted within a joint through tissue surrounding the joint. The drill bit is provided with a cavity to receive the end of a drill drive shaft. Depending on the desired direction of drilling, the cavity is located at one end or the other of the drill bit. The drill bit additionally includes a recess for receiving the end of a removable fixation device which permits the drill bit to be held in position while the drive shaft is being locked or unlocked from the drill bit's cavity.

BRIEF DESCRIPTION OF THE DRAWINGS

The invention now will be described in greater detail with respect to the accompanying drawings wherein:

FIGS. 4A–G diagrammatically illustrate the present invention used in a retrograde drilling operation within a joint; and FIGS. 5A–F diagrammatically illustrate the present invention used in an antegrade drilling operation within a joint.

DETAILING DESCRIPTION OF THE PREFERRED EMBODIMENTS OF THE INVENTION

Figure 1:
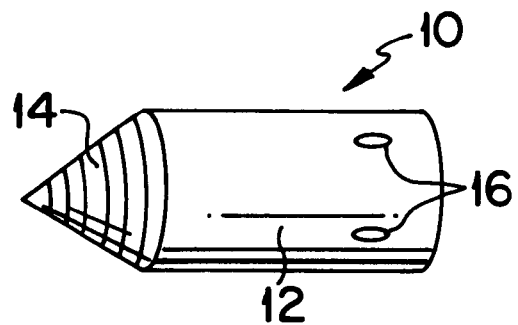
FIG. 1 is a side elevational view of a drill bit according to the invention.

Referring to the drawings, FIG. 1 illustrates a drill bit 10 having a base portion 12 and a tapered drilling portion 14. At least one recess 16 is provided in base portion 12 for receiving a removable fixation device which hereinafter will be described. The drilling portion 14 is illustrated as having a twist type drilling thread on its exterior. It will be understood, however, that portion 14 may be adapted for compaction or Forestner type drilling.

Drill bit 10 is dimensioned to fit within a joint. For example, for ligament reconstruction surgery a typical length of the drill bit is 2 cm.

Figure 2:
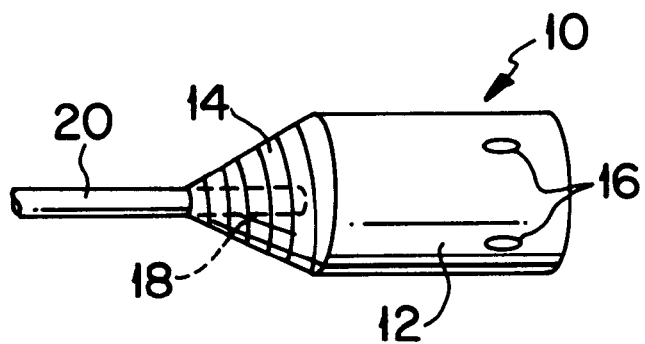
FIG. 2 is a side elevational view of a drill bit shaft joined to one end of the drill bit shown in FIG. 1.

The drill bit additionally is provided with a cavity to receive the end of drill drive shaft. FIG. 2 illustrates a bit 10 having a cavity 18 which is coaxial with the longitudinal axis of the bit and is located in the drilling portion of the bit. Cavity 18 is shown receiving the end of drive shaft 20. Such an arrangement permits retrograde drilling within the joint as will be described hereinafter with respect to FIGS. 4A–4G. Typically, the end of shaft 20 is threaded so as to cooperate with threads provided on the wall of cavity 18. However, other known arrangements for securing the end of shaft 20 within cavity 18 could be employed.

Figure 3:
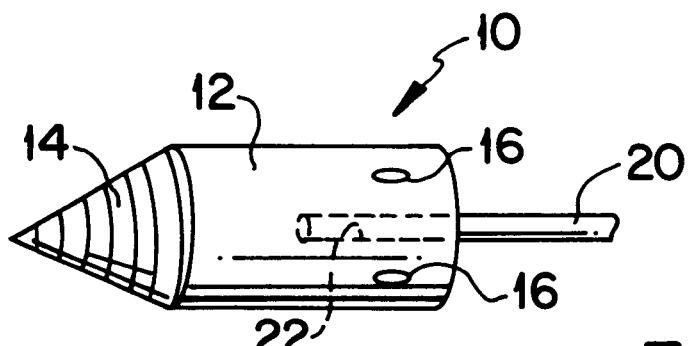
FIG. 3 is a side elevational view of a drill shaft joined to the opposite end of the drill bit shown in FIG. 1.

FIG. 3 illustrates drill bit 10 as configured for antegrade drilling. More particularly, a cavity 22 is formed in base portion 12 coaxially with the longitudinal axis of the bit. Cavity 22 receives the end of the drill drive shaft 20 in the same manner described with respect to FIG. 2 Although FIGS. 2 and 3 illustrate different bits 10 for use respectively in retrograde and antegrade drilling, it will be understood that a single bit 10 can be provided with cavities 18 and 22 at opposite ends thereof so as to permit the bit to be used for either type of drilling.

Retrograde drilling now will be described with respect to FIGS. 4A to 4G which illustrate a typical bone joint within which drilling is to be performed. For convenience of illustration the drill which powers the drill drive shaft 20 has been omitted.

In FIG. 4A, drive shaft 20 is passed through a narrow passageway which the surgeon has formed in one of the bones to permit the free end of drive shaft 20 to enter the joint. The surgeon then inserts bit 10 within the joint by passing it through surrounding tissue, and a removable fixation device 24 is inserted within a recess 16 in the base portion of the bit. Preferably the device 24 is a rod used to orient the bit relative to the end of the shaft 20 and to retain bit 10 while shaft 20 is secured within cavity 18 of the bit (FIG. 4B). However, other suitable devices, such as a clamp, could be used instead of a rod. Once the drive shaft 20 is secured, fixation rod 24 is removed and the drill is actuated to move the bit 10 into contact with the bone which has received shaft 20. The bore formed by the surgeon for drive shaft 20, and the shaft itself, serve to guide the drill bit as it moves within the bone (FIGS. 4C and 4D). When the desired cavity 26 is formed in the bone, drive shaft 20 is displaced along its bore to return bit 10 to the joint. At this point, fixation rod is again inserted within a recess 16 in the base portion of the bit to permit shaft 20 to be released from the bit followed by removal of the shaft and the bit from the joint (FIGS. 4E and 4F). This completes the retrograde drilling operation and leaves cavity 26 in readiness for the next step in the surgical procedure (FIG. 4G).

Antegrade drilling will now be described with reference to FIGS. 5A to 5F. Again, for convenience of illustration, the drill for powering the drill shaft has been omitted.

As in the case of retrograde drilling, the drill bit 10 is positioned within the joint by being passed through surrounding tissue, and fixation rod 24 is inserted within a recess 16 in the base portion of the bit (FIG. 5A). The rod 24 is used to orient and retain the bit while the end of shaft 20 is secured within cavity 22 of the bit (FIG. 5B). Rod 24 is then removed, and the bit 10 is advanced within the adjacent bone in the direction indicated by the arrow (FIG. 5C). When the desired cavity 28 has been formed in the bone, the bit and shaft are withdrawn (FIG. 5D), and the fixation rod 24 is reinserted into a recess 16 in the base portion of the bit to permit the shaft 20 to be disengaged from the bit (FIG. 5E). The bit 10 and fixation rod 24 are then removed from the joint so that the surgeon can proceed using cavity 28 (FIG. 5F).

What is claimed is:

1. An intra-articular drill for forming a cavity in bone from with a joint, comprising:

a drill bit dimensioned to be received within said joint and having a base portion at a proximal end and a drilling portion at a distal end;

a recess formed in said drill bit in coaxial relationship with a longitudinal axis of the drill bit, said recess being formed in said drilling portion of the drill bit commencing at the distal end thereof; and a drill shaft having an end portion adapted to be introduced within, secured to, and released from the recess from the distal end of the drill bit.

2. An intra-articular drill according to claim 1, further comprising:

fixation means removably connected to said drill bit for orienting and retaining the position of the drill bit within the joint, said fixation means including a rod having an end adapted to be removably inserted in a further recess provided in a side surface of said base portion of the drill bit.

3. An intra-articular drill according to claim 1, further comprising:

an additional recess formed in said drill bit in coaxial relationship with said longitudinal axis, said additional recess being formed in the base portion of the drill bit commencing at the proximal end thereof and being adapted to receive and retain said end portion of the drill shaft.

4. An intra-articular drill according to claim 7, further comprising:

fixation means removably connected to said drill bit for orienting and retaining the position of the drill bit within the joint, said fixation means including a rod having an end adapted to be removably inserted in a still further recess provided in a side surface of said base portion of the drill bit.

\* \* \* \* \*